(12) United States Patent
Geckeler et al.

(10) Patent No.: US 7,534,944 B2
(45) Date of Patent: May 19, 2009

(54) CARBON NANOTUBE FUNCTIONALIZED WITH OSMIUM CLUSTERS AND PROCESS FOR PREPARING SAME

(75) Inventors: Kurt E. Geckeler, Gwangju (KR); Dhriti Nepal, Gwangju (KR); Edward Rosenberg, Missoula, MT (US)

(73) Assignee: Gwangju Institute of Science and Technology (KR)

( * ) Notice: Subject to any disclaimer, the term of this patent is extended or adjusted under 35 U.S.C. 154(b) by 528 days.

(21) Appl. No.: 11/300,022

(22) Filed: Dec. 13, 2005

(65) Prior Publication Data

US 2007/0157347 A1 Jul. 5, 2007

(30) Foreign Application Priority Data

Dec. 13, 2004 (KR) .................... 10-2004-0104924

(51) Int. Cl.
*D01F 9/12* (2006.01)
(52) U.S. Cl. .................... 977/748; 423/447.2; 423/460; 977/847
(58) Field of Classification Search ............. 423/447.1, 423/447.2, 460, 445 B; 977/742, 745, 842, 977/847, 746, 748
See application file for complete search history.

(56) References Cited

U.S. PATENT DOCUMENTS

2007/0145335 A1* 6/2007 Anazawa et al. ............ 252/500

OTHER PUBLICATIONS

Cui et al., "Reversible Sidewall Osmylation of Individual Carbon Nanotubes," 2003, Nano Letters, vol. 3, No. 5, pp. 613-615.*
Lu et al. "Sidewall Oxidation and Complexation of Carbon Nanotubes by Base-Catalyzed Cycloaddition of Transition Metal Oxide: A Theoretical Prediction," 2002, vol. 2, No. 11, pp. 1325-1327.*
Smith et al., "Reactivity of Electron Deficient Benzoheterocycle Triosmium Clusters, 5. The Chemistry of Os3(CO)9(us-n2-(C(9)-N)-5,6-benzoquinolyl)(u-H) and Its Phosphine Derivative," 1999, Organometallics, 18, pp. 3519-3527.*
Park et al., "Triosmium Cluster Derivatives of [6OIFullerene," 1995, J. Chem. Soc., Chem. Commun., pp. 15-16.*
Hongjie Dai, Carbon Nanotubes: Synthesis, Integration, and Properties, Acc. Chem. Res. 2002, 35, 1035-1044.
Sarbajit Banerjee, et al., Selective Metallic Tube Reactivity in the Solution-Phase Osmylation of Single-Walled Carbon Nanotubes, J.Am.Chem.Soc. 2004, 126, 2073-2081.
E. Rosenberg, et al., Synthesis, characterization and DNA binding affinities of water-soluble benzoheterocycle triosmium clusters, Jour of Organometallic Chem 668 (2003) 51-58.

(Continued)

*Primary Examiner*—Wayne Langel
*Assistant Examiner*—Brittany M Martinez
(74) *Attorney, Agent, or Firm*—Baker & Hostetler, LLP (57) ABSTRACT

The osmium (Os) cluster-functionalized CNT of the present invention formed from a triosmium derivative having one or more amine groups and a functionalized carbon nanotube having a plurality of COOH groups through zwitterionic interactions between the COOH and amine groups has high solubilities in water and various organic solvents.

9 Claims, 10 Drawing Sheets

OTHER PUBLICATIONS

Xin Lu, et al., Sidewall Oxidation and Complexation of Carbon Nanotubes by Base-Catalyzed Cycloaddition of Transistion Metal Oxide . . . , Nano Letters 2002 vol. 2, No. 11, 1325-27.

Jingbiao Cui, et al., Reversible Sidewall Osmylation of Individual Carbon Nanotubes, Nano Letters 2003, vol. 3, No. 5, 613-615.

* cited by examiner

CARBON NANOTUBE FUNCTIONALIZED WITH OSMIUM CLUSTERS AND PROCESS FOR PREPARING SAME

FIELD OF THE INVENTION

The present invention relates to a novel carbon nanotube functionalized with osmium clusters, and a process for preparing the same.

DESCRIPTION OF THE PRIOR ART

Carbon nanotubes (CNTs) are classified into single walled nanotubes (SWNTs), multi-walled nanotubes (MWNTs) and rope nanotubes, and possess outstanding physical, chemical and mechanical properties, such as lightweight, excellent electrical and thermal conductivity and high tensile force.

In particular, CNTs exhibit either condutivity or semiconductivity depending on their surroundings through selective reactions with specific target molecules and thus are suitable for nanoscale sensing materials or nano-bioelectronic device applications. In this regards, in order to enhance such selectivities of CNTs, there have been developed functionalization or bio-immobilization techniques to anchor functional groups to CNTs so that the functionalized CNTs can selectively react with specific target molecules (H. Dai, *Acc. Chem. Res.*, 35, 1035 (2002)).

Osmium (Os) clusters having good electrochemical properties are often used in nuclear energy, sensing system and molecular electronic applications. Recently, the synthesis of an Os cluster derivative comprising a specific DNA binding site has been reported (E. Roseberg et al., *J. Organometal Chem.*, 668, 51(2003)). Also, there have been numerous attempts to combine a CNT with such a specific Os cluster; for example, osmylation of SWNT by photoactivation reaction using $OsO_4$ (Cui, J. at al., *Nano Lett.*, 3, 615 (2003)); osmate esterification of SWNT (Lu, X. et al., *Nano Lett.*, 2, 1325 (2002)); and interaction of liquid-phase $OsO_4$ with SWNT under UV irradiation (Banerjee, S. et al., *J. Am. Chem. Soc.*, 126, 2073-2081 (2004)). However, such Os-CNT complexes all have low solubilities in water and organic solvents, to limit their industrial applications.

The present inventors have endeavored to develop a CNT-Os cluster complex having high solubilities in water and organic solvents; and have unexpectedly found that a new kind of Os cluster-functionalized CNT has high solubilities in organic solvents as well as water.

SUMMARY OF THE INVENTION

Accordingly, it is a primary object of the present invention to provide a functionalized carbon nanotube (CNT) which is highly soluble in water and various organic solvents.

It is another object of the present invention to provide an efficient process for the preparation of said CNT.

In accordance with one aspect of the present invention, there is provided an Os cluster-functionalized CNT complex formed from a triosmium derivative having one or more amine groups and a functionalized carbon nanotube having a plurality of COOH groups through zwitterionic interactions between the COOH and amine groups.

In accordance with another aspect of the present invention, there is provided a method for preparing said Os cluster-functionalized CNT, which comprises reacting the carboxyl (COOH)-functionalized CNT with the amino-functionalized triosmium derivative in an organic solvent.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The inventive osmium cluster-functionalized CNT is a zwitterion complex formed between the CNT and Os cluster through ammonium-carboxylate bond ($—CO_2^{-+}NH_3—$).

The inventive osmium cluster-functionalized CNT may be prepared by the method comprising the step of reacting the carboxyl-functionalized CNT with the amino-functionalized triosmium derivative in an organic solvent under a nitrogen atmosphere.

The carboxyl-functionalized CNT used in the present invention may be obtained by oxidizing a CNT with a concentrated inorganic acid according to a conventional method (J. Liu et al., *Science*, 280, 1253-1256 (1998); and the amino-functionalized triosmium derivative, by reacting a triosmium cluster with an aminated benzoquinoline in accordance with a conventional method (R. Smith et al., *Organometallics*, 18, 3519-3527 (1999)).

The inorganic acid suitable for use in the oxidation of CNT include nitric acid, hydrochloric acid and a mixture of sulfuric acid and nitric acid, which may be employed in an amount ranging from 1 to 10 ml based on 10 mg of CNT. The oxidation of CNT may be conducted at a temperature ranging from 40 to 90° C. for 2 to 8 hours.

In the inventive method, the amino-functionalized triosmium derivative may be used in an amount ranging from 1 to 2 times, preferably 2 times the weight of the carboxyl-functionalized CNT, and the organic solvent may be selected from the group consisting of N,N-dimethyl formamide (DMF), dimethylsulfoxide (DMSO), acetone and octane. The reaction may be carried out at a temperature ranging from 70 to 140° C. for 3 to 7 days.

The inventive osmium cluster-functionalized CNT thus prepared has high solubilities in water and various organic solvents, and is easy to handle. Therefore, the inventive CNT can be advantageously used in CNT-based catalytic processes and next-generation electronic devices including nanobio-electronic devices.

The following Examples are given for the purpose of illustration only and are not intended to limit the scope of the invention.

Preparation of Inventive Compounds

EXAMPLE 1

Preparation of an Osmium Cluster-functionalized CNT

A purified single walled nanotube (SWNT; Ilzin, KR) was grown on a silicon substrate by pulsed laser deposition (PLD) according to the Fe catalyst-CNT growing method described in [Sohn, J. I. et al., *App. Phy. Let.*, 78, 901-903 (2001)], to obtain a multi-walled nanotube (MWNT) having a high purity of 95%. 10 mg of the MWNT was treated with 10 ml of concentrated $HNO_3$ at 80° C. for 6 hours, and the resulting oxidized MWNT was washed and dried. 20 mg of an aminated compound of the following formula obtained by the method described in [R. Smith et al., *Organometallics*, 18, 3519-3527 (1999)] was added dropwise thereto under a nitrogen atmosphere, and the mixture was continuously stirred at 140° C. for 7 days.

After the color of the reaction mixture changed from green to brown, the reaction mixture was centrifuged and the liquid phase was removed. The resulting solid was sequentially washed several times with water and acetone, and dried in a vacuum oven to obtain 5 mg (yield 50%) of the title compound.

EXAMPLE 2

Preparation of an Osmium Cluster-functionalized CNT

The procedure of Example 1 was repeated except for using concentrated HCl instead of concentrated $HNO_3$, to obtain 5 mg (yield 50%) of the title compound.

Characteristics of Inventive Compounds (1) IR and Mid-IR Spectra

Figure 1:
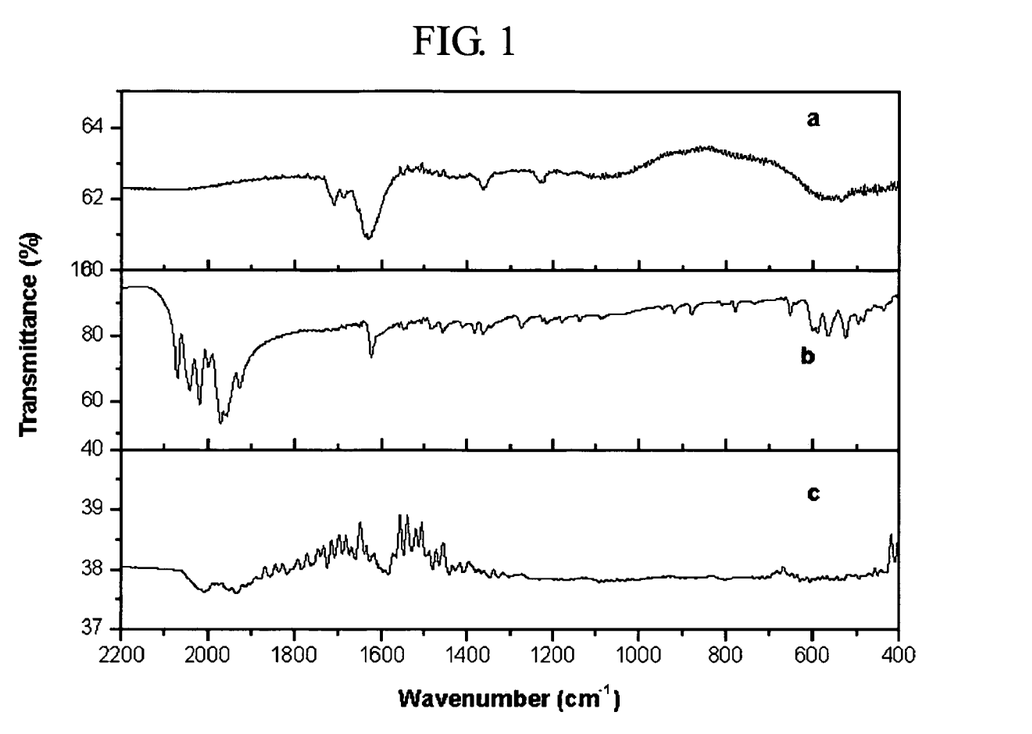
FIG. 1: Infrared (IR) spectra of the oxidized CNT (a), triosmium derivative (b) and osmium cluster-CNT prepared in Example 1 (c)
Figure 2:
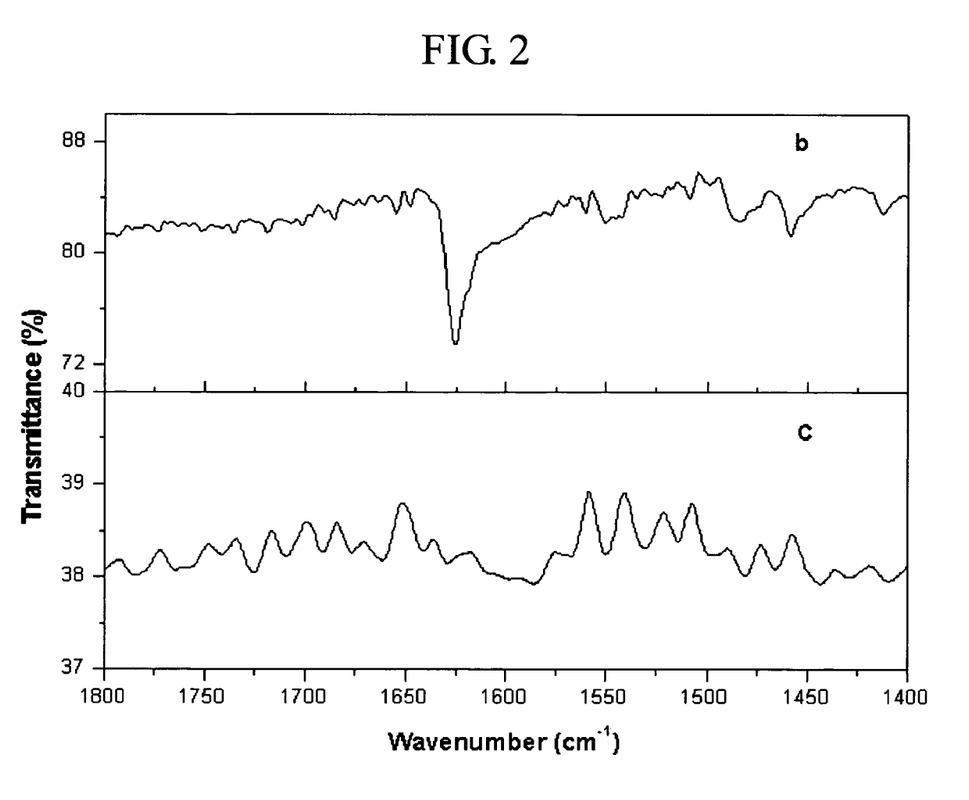
FIG. 2: Mid-IR spectra of the triosmium derivative (b) and osmium cluster-CNT prepared in Example 1 (c)

IR and Mid-IR spectra of the oxidized CNT (a), amino-functionalized triosmium derivative (b) and osmium cluster-functionalized CNT prepared in Example 1 (c) are shown in FIGS. 1 and 2, respectively. The wavenumbers of characteristic peaks observed in FIGS. 1 and 2 are listed in Table 1, respectively.

TABLE 1

|  | CNT-COOH (a) | Os derivative (b) | CNT-Os complex (c) |
|---|---|---|---|
| ν OH (carboxyl group) | 3228 cm$^{-1}$ |  |  |
| Y C=O | 1712 cm$^{-1}$ |  |  |
| ν C—O | 1233 cm$^{-1}$ |  |  |
| ν N—H |  | 1625 cm$^{-1}$ | 1629, 1550 cm$^{-1}$ |
| ν C—N |  | 1274 cm$^{-1}$ | 1278 cm$^{-1}$ |
| C=O (carboxylic acid) |  |  | 1585 cm$^{-1}$ |

The results in Table 1 show that the preparations of the desired oxidized CNT, amino-functionalized triosmium derivative and Os cluster-functionalized CNT were indeed achieved, as is supported by the following discussion.

Referring to FIGS. 1 and 2, the strong peaks at 1712 cm$^{-1}$ (C=O) and 1233 cm$^{-1}$ (C—O) observed for the oxidized CNT were absent in the spectrum of the Os cluster-functionalized CNT, and broad strong peaks representing N—H bond were detected at 1625 cm$^{-1}$ in the spectrum of the triosmium derivative and at 1629 cm$^{-1}$ in the spectrum of the Os cluster-functionalized CNT. Further, a strong symmetrical COO$^-$ peak at 1585 cm$^{-1}$, a broad peak corresponding to C—N bond at 1278 cm$^{-1}$ (in case of triosmium derivative at 1274 cm$^{-1}$), and osmium peaks at 1933 cm$^{-1}$ and 2023 cm$^{-1}$ were observed in the spectrum of the Os cluster-functionalized CNT.

Accordingly, it can be deduced that the Os cluster-functionalized CNT prepared above is a zwitterion complex formed between the CNT and Os cluster through ammonium-carboxylate bond ($—CO_2^{-+}NH_3—$).

(2) UV-Vis-NIR Spectra

Figure 3:
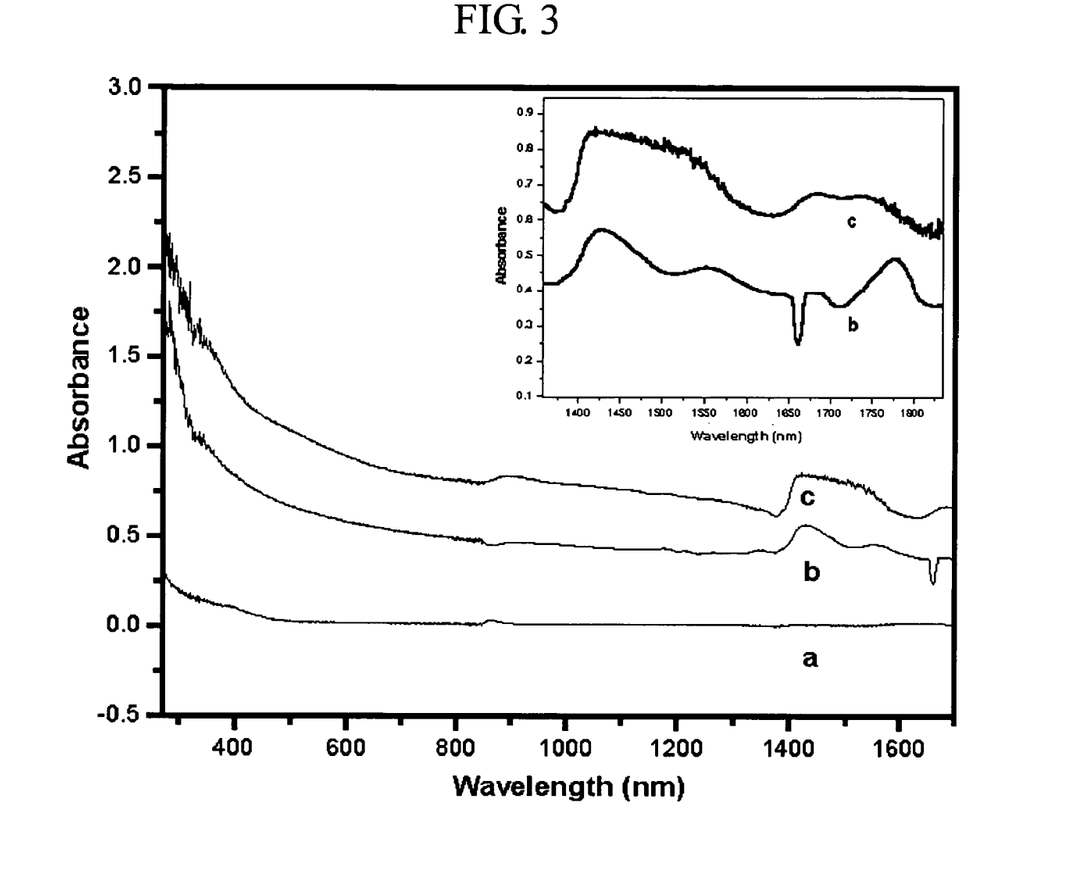
FIG. 3: UV-Vis-NIR spectra of the triosmium derivative (a), oxidized CNT (b) and osmium cluster-CNT prepared in Example 1 (c)
Figure 4A:
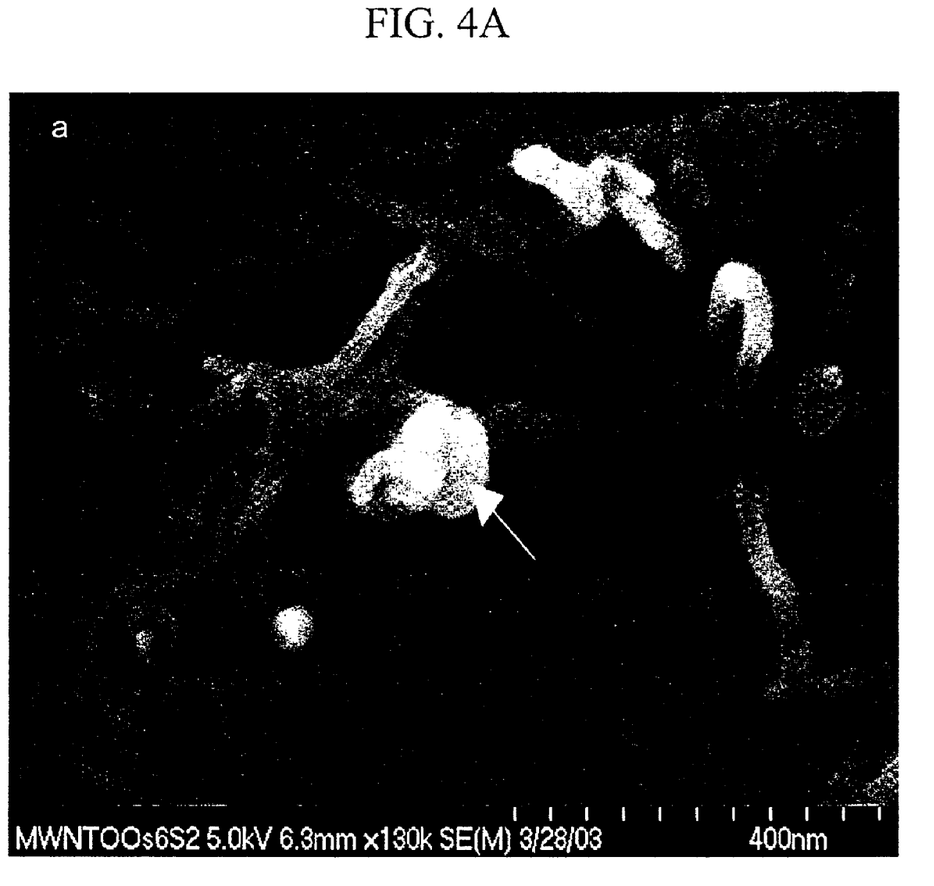
FIGS. 4A to 4D: Scanning electron microscopy (SEM) images of the osmium cluster-CNT prepared in Example 1 (FIGS. 4A to 4C) and CNT (FIG. 4D)
Figure 4B:
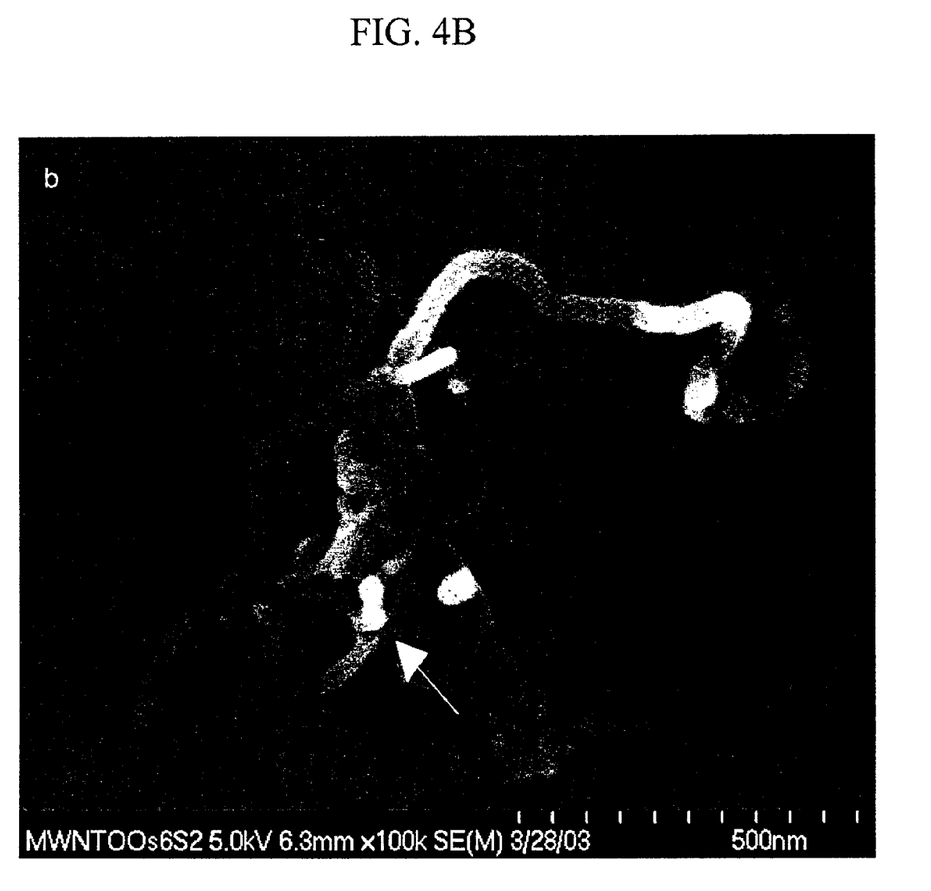
Figure 4C:
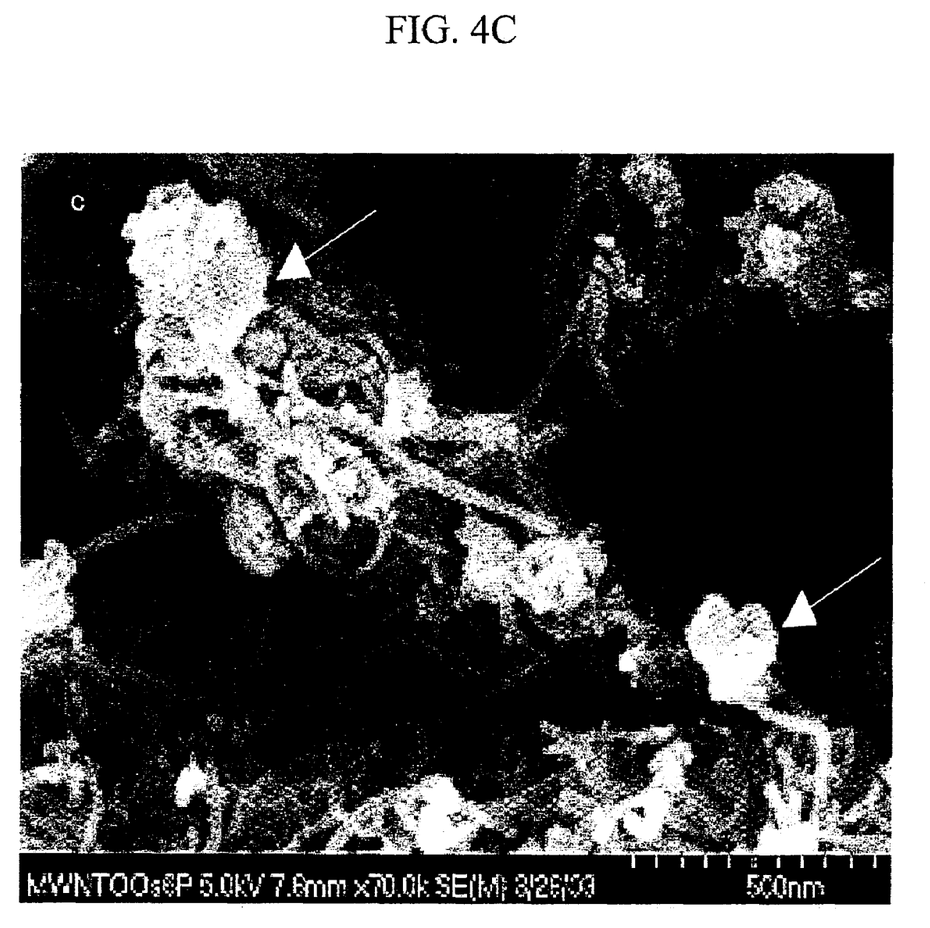
Figure 4D:
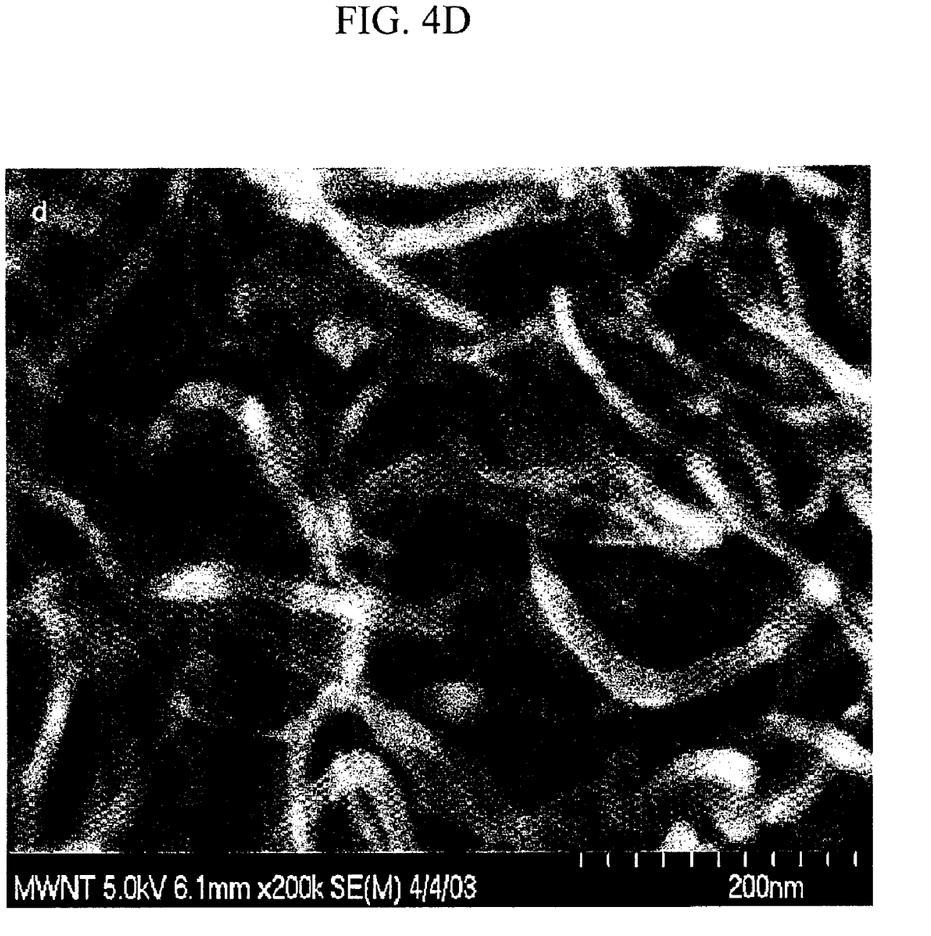

UV-Vis-NIR spectra of the amino-functionalized triosmium derivative (a), oxidized CNT (b) and osmium cluster-functionalized CNT prepared in Example 1 (c) are shown in FIG. 3 (the inset shows partially enlarged portion of the spectrum).

Referring to the results in FIG. 3, two main peaks at 1414 nm (1.14 eV) and 1554 nm (1.24 eV) in the spectrum of Os cluster-functionalized CNT are similar to those observed in the spectrum of oxidized CNT, which suggests that the inventive Os cluster-functionalized CNT has an intact carboxylate group of the CNT moiety linked to the Os cluster through an ionic ammonium-carboxylate bond. Further, the small peak observed at 859 nm (1.44 eV) in the spectrum of amino-functionalized tri-Os derivative is red-shifted 890 nm in the spectrum of Os cluster-functionalized CNT, which means that the conjugation length between the Os and amino group has increased due to the formation of the ammonium-carboxylate bond.

(3) SEM, TEM and EDX Spectra

Figure 5A:
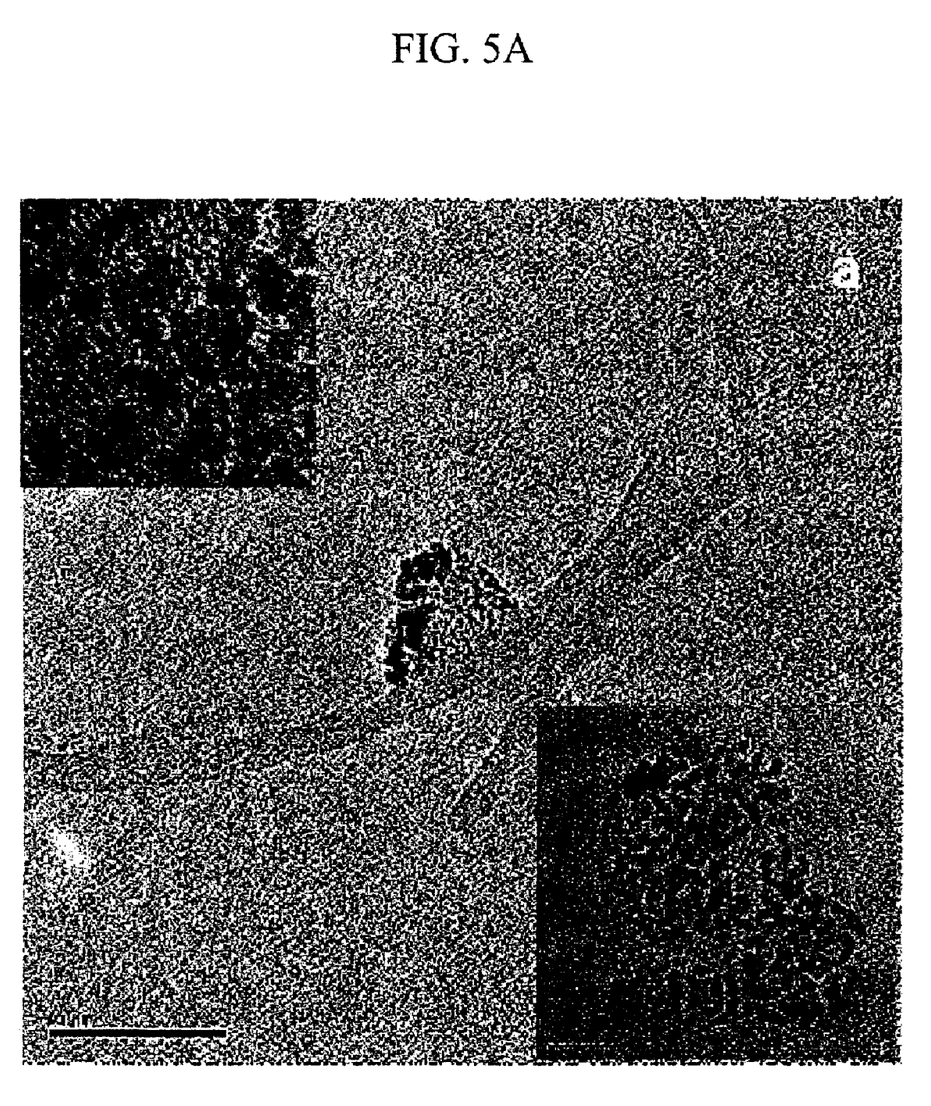
FIGS. 5A and 5B: Transmission electron microscopy (TEM) images of the osmium cluster-CNT prepared in Example 1.
Figure 5B:
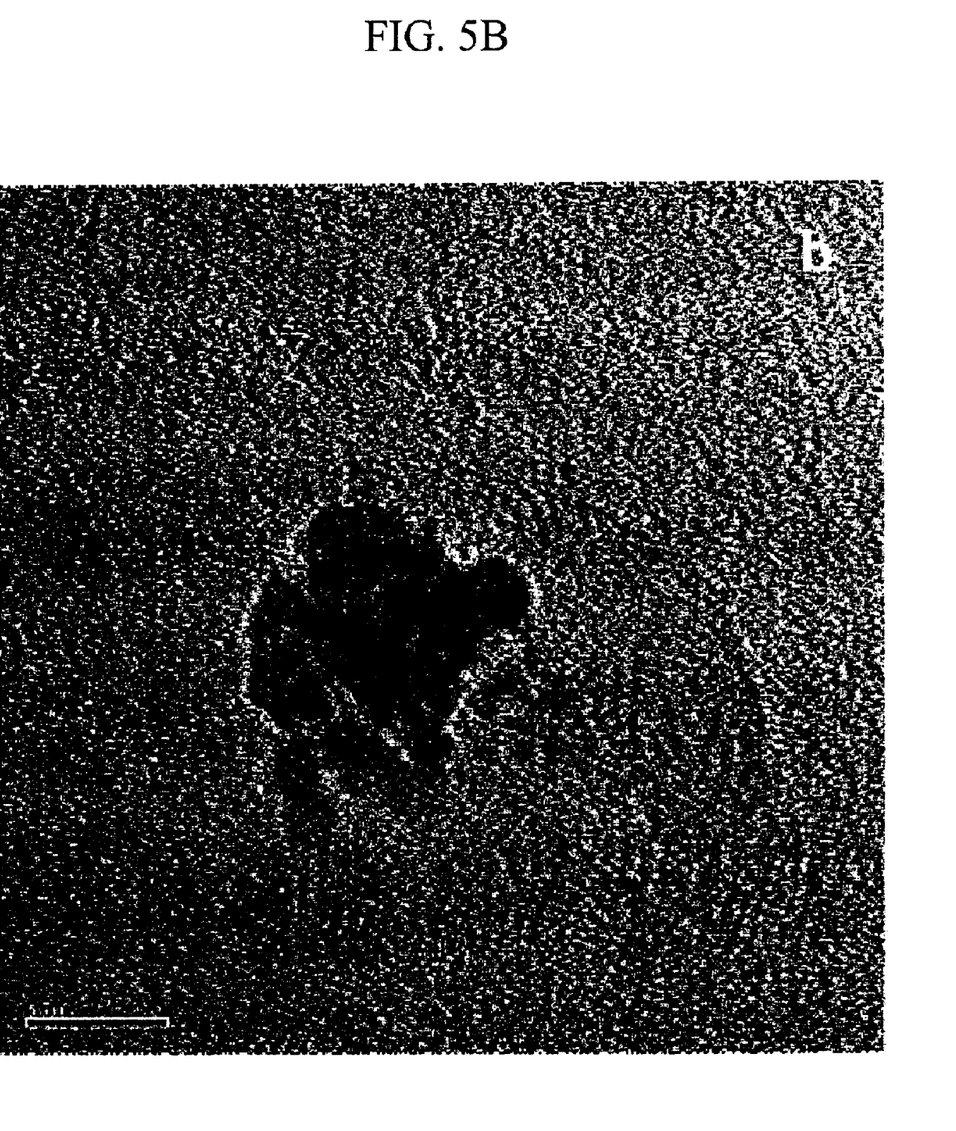

The detail morphological properties of the Os cluster-functionalized CNT obtained in Example 1 and pristine CNT were evaluated by SEM (FIGS. 4A to 4D) and TEM (FIGS. 5A and 5B).

FIGS. 4A to 4D clearly show that bulky groups are attached on the tips of the tubes having lengths of 30 nm to 1.5 μm of the Os cluster-functionalized CNT (4A to 4C), unlike in the pristine CNT (4D), which demonstrates the zwitterion formation between CNT and Os derivative. Further, the bulky groups are not formed on the sidewalls of the same tubes because COOH groups mainly exist on the tips rather than sidewalls.

Figure 6:
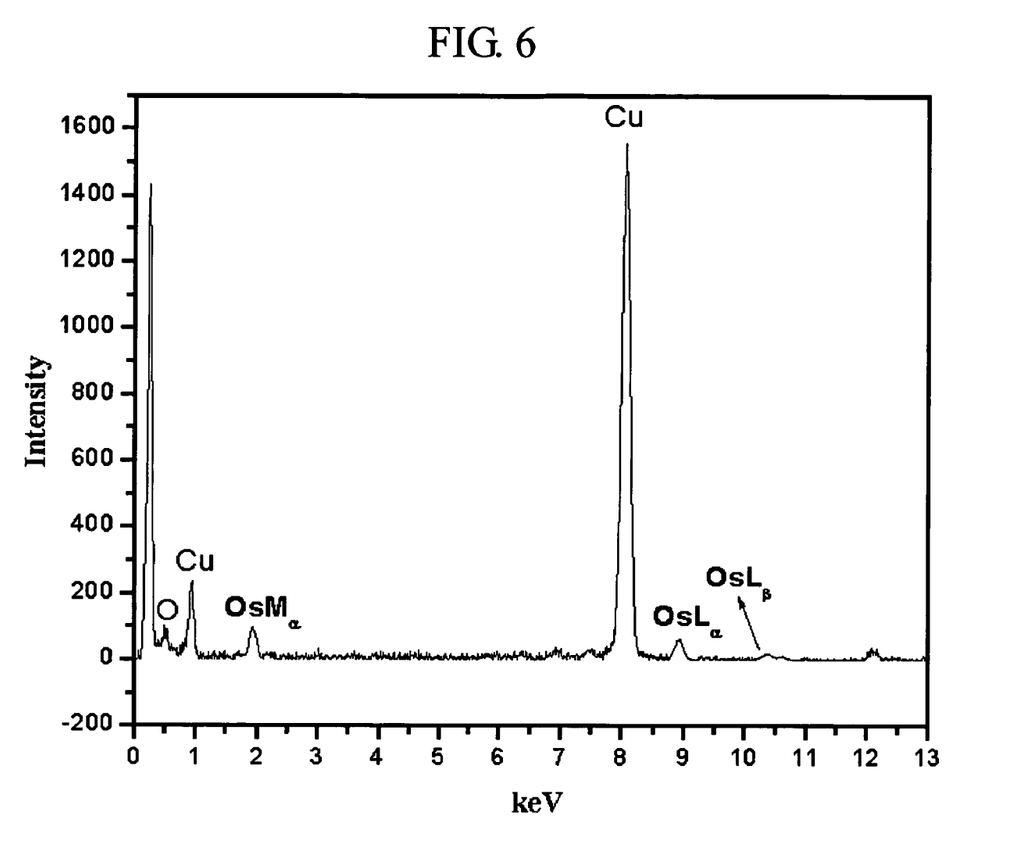
FIG. 6: Energy dispersive X-ray spectrum (EDX) of the osmium cluster-CNT prepared in Example 1.

FIG. 6 shows EDX spectra of the Os cluster-functionalized CNT obtained in Example 1, which suggests that Os groups occupy about 1.4% of the functional moieties in the Os cluster-functionalized CNT.

(4) Measurement of Solubility

The solubilities of the oxidized and Os cluster-functionalized CNTs in water, DMF, THF and DMSO were measured.

It was found that the Os cluster-functionalized CNT had the solubilities of 150 mg/L in water, 250 mg/L in DMF, 50 mg/L in THF and 250 mg/L in DMSO. While the pristine CNT was hardly soluble in any of the solvents, the oxidized CNT had the solubilities of 7 mg/L in DMF, 7 mg/L in DMSO and 4 mg/L in THF. Thus, it can be seen that the inventive Os cluster-functionalized CNT has high solubilities in industrially useful organic solvents as well as in water due to the characteristic zwitterion bond.

Accordingly, the novel CNT functionalized with Os cluster of the present invention can be advantageously used in various fields including CNT-based catalytic processes and nano-bioelectronic devices.

While the invention has been described with respect to the specific embodiments, it should be recognized that various modifications and changes may be made by those skilled in the art to the invention which also fall within the scope of the invention as defined by the appended claims.

What is claimed is:

1. A method for preparing an osmium (Os) cluster-functionalized carbon nanotube (CNT) complex which comprises the steps of: reacting a COOH-functionalized CNT with an amino-functionalized triosmium derivative to make ammonium-carboxylate bond (—CO2−+NH3-) between the amine and COOH groups through zwitterion interaction.

2. The method of claim 1, wherein the COOH-functionalized CNT and the triosmium derivative are reacted in an organic solvent.

3. The method of claim 1, wherein the COOH-functionalized CNT is prepared by oxidizing a CNT with a concentrated inorganic acid.

4. The method of claim 3, wherein the inorganic acid is nitric acid, hydrochloric acid, or a mixture of sulfuric acid and nitric acid.

5. The method of the claim 1, wherein the amino-functionalized triosmium derivative is prepared by reacting a triosmium cluster with an aminated benzoquinoline.

6. The method of claim 1, wherein the amino-functionalized triosmium derivative is used in an amount ranging from 1 to 2 times the weight of the COOH-functionalized CNT.

7. The method of claim 2, wherein the organic solvent is selected from the group consisting of N,N-dimethyl formamide (DMF), dimethylsulfoxide (DMSO), acetone and octane.

8. The method of the claim 1, wherein the reaction is carried out at a temperature ranging from 70 to 140° C.

9. An osmium (Os) cluster-functionalized carbon nanotube (CNT) complex comprising triosmium derivative having one or more amine groups and CNT having a plurality of COOH groups, wherein zwitterion interaction between the amine and COOH groups makes ammonium-carboxylate bond (—CO2−+NH3-).

* * * * *